(12) United States Patent
Novak et al.

(10) Patent No.: US 9,752,868 B2
(45) Date of Patent: Sep. 5, 2017

(54) OPTICAL MEASUREMENT OF LEAD ANGLE OF GROOVE IN MANUFACTURED PART

(71) Applicants: Erik Novak, Tucson, AZ (US); Florin Munteanu, Livermore, CA (US)

(72) Inventors: Erik Novak, Tucson, AZ (US); Florin Munteanu, Livermore, CA (US)

(73) Assignee: BRUKER NANO INC., Santa Barbara, CA (US)

( * ) Notice: Subject to any disclaimer, the term of this patent is extended or adjusted under 35 U.S.C. 154(b) by 0 days.

(21) Appl. No.: 15/289,127

(22) Filed: Oct. 8, 2016

(65) Prior Publication Data

US 2017/0023356 A1 Jan. 26, 2017

Related U.S. Application Data

(63) Continuation-in-part of application No. 12/916,252, filed on Oct. 29, 2010, now abandoned.

(51) Int. Cl.
*G01B 11/24* (2006.01)
*G01B 11/26* (2006.01)
*G05B 19/418* (2006.01)

(52) U.S. Cl.
CPC .......... *G01B 11/2441* (2013.01); *G01B 11/26* (2013.01); *G05B 19/41875* (2013.01)

(58) Field of Classification Search
CPC ..... G01B 11/02; G01B 11/24; G01B 11/2441; G01B 11/26
See application file for complete search history.

(56) References Cited

U.S. PATENT DOCUMENTS

| 5,398,113 | A | * | 3/1995 | de Groot | G01B 11/2441 356/497 |
|---|---|---|---|---|---|
| 5,633,715 | A | * | 5/1997 | Ai | G01B 9/02057 356/497 |
| 7,327,469 | B2 | * | 2/2008 | Deck | G01B 11/2441 356/511 |
| 8,132,802 | B2 | * | 3/2012 | Kolodge | G01B 11/2425 250/559.19 |
| 2005/0151978 | A1 | * | 7/2005 | Nakamura | G02B 21/002 356/602 |
| 2005/0174567 | A1 | * | 8/2005 | Hanna | G01N 21/952 356/237.1 |
| 2009/0103111 | A1 | * | 4/2009 | Spalding | G01B 11/245 356/638 |

\* cited by examiner

*Primary Examiner* — Manuel L Barbee
(74) *Attorney, Agent, or Firm* — Antonio R. Durando (57) ABSTRACT

A portion of the surface of a cylindrical part with a machined groove is mapped with an optical profilometer during the manufacturing process and the height map is fitted to a virtual cylindrical configuration that best fits the data. Two-dimensional Fourier Transfer analysis of the map data is advantageously used to find the orientation of the groove on the part. The orientation of the groove is then compared to the longitudinal axis of such virtual cylinder to calculate the groove's lead angle. If the measured lead angle is outside a predetermined design tolerance deemed acceptable for manufacturing purposes, the part is removed from the fabrication line.

27 Claims, 6 Drawing Sheets

OPTICAL MEASUREMENT OF LEAD ANGLE OF GROOVE IN MANUFACTURED PART

REFERENCE TO RELATED APPLICATIONS

This application is a continuation-in-part application of Ser. No. 12/916,252, filed Oct. 29, 2010, hereby incorporated by reference in its entirety.

BACKGROUND OF THE INVENTION

Field of the Invention

This invention pertains to the general field of optical metrology. In particular, it pertains to a novel method and apparatus for measuring the orientation of machined grooves in manufactured parts f or the purpose of quality control during the manufacturing process.

Description of the Prior Art

Many industrial parts are manufactured or finished by a process where a cutting tool removes material from the part, thereby shaping it and/or smoothing it. Milling, turning, grinding, and boring are such machining processes where the motions of the cutting tool and the workpiece relative to each other, referred to in the art as "feed" and "cutting speed," respectively, produce the finished part. The shape of the tool and its penetration into the surface of the workpiece, combined with these motions, yield the desired shape of the resulting work surface.

In the formation of finite surfaces, some form of turning and translating of a single cutting edge or broad contact area are used to remove material from a rotating workpiece. While the workpiece rotates, the cutting tool moves slowly in a predetermined direction and removes material from the surface of the rotating workpiece. In more complex cases, the translation in the predetermined direction can be associated with a secondary translation in a perpendicular direction in order to accommodate more advanced geometries. As the contact area is from one or more locations on the machining tool, the tool necessarily leaves one or more grooves on the workpiece. The groove or grooves lie in a plane substantially normal to the main axis of the part (around which the part is rotated during milling), but not exactly so because the advancing feed motion of the cutting tool and the rotational speed during milling necessarily produce a groove orientation with a particular angle with respect to the axis of rotation. In fact, the grooves substantially define a helix characterized, by definition, by the fact that the tangent line at any point makes a constant angle with the main axis of the part. In the context of machining grooves, this angle is normally referred to as the lead angle of the groove or lead mark. In many cases, the angle is desired to be as close to perpendicular to the rotational axis as possible, while in other cases a specific direction of the grooves is desired, such as to ensure material always flows in one direction as the part is actuated in its final application.

When a cylindrical part so produced is used in a lubricated rotating application, such as in a bearing, the presence of grooves that are not perfectly perpendicular to the axis of rotation produces a pumping action that transports the lubricant from one side of the part to the other, thereby either depleting the lubricant from its operating environment or introducing a foreign fluid from the exterior, depending, as one skilled in the art will readily understand, on the direction of rotation of the part and the orientation of the groove relative thereto. In either case, this is a problem that can be serious in applications where the retention of uncontaminated lubricant is critical, as in automotive applications. The presence of seals is typically not sufficient to overcome this problem.

Therefore, during the manufacturing of these parts, it has become important to measure key properties of these grooves, including lead angle, depth, orientation, and frequency to ensure that they are kept within acceptable tolerances for the particular application of interest. (Note that a minimal lead angle is unavoidable in a part finished with a lathe because of the feed motion of the cutting tool.) If the angle is not within a predetermined tolerance of a design value, for instance, the manufacturing process is stopped and the part is removed from the process and is either discarded or re-machined, as may be appropriate, after calibration or repair as of the cutting tool. Among the methods used to measure tolerance parameters, for example, the automotive industry has relied on a simple technique applicable only to cylindrical parts. It consists of placing a thin string or thread in the groove of the perfectly horizontal part, rotating the part, and measuring the axial shift of the thread after a known number of rotations. (See http://www.bsahome.org/tools/pdfs/Wear_Sleeves_web.pdf.) From this information and from the knowledge of the dimensions of the part, the angle of the groove with respect to the part's axis is easily calculated. For instance, if a part with diameter D shows an axial shift/of the thread placed in the groove for each turn of the part (i.e., the pitch of the helix defined by the groove), the angle of the groove with respect to the part's axis will be easily calculated as arcsin(2l/D). (While this relation is not exact, one skilled in the art will appreciate that it is nonetheless a very close approximation for small angles.)

However, this simple measurement technique can only work for cylindrical parts when the groove is pronounced enough to hold and translate the measurement thread, which is not always the case and is rarely so for parts intended to be perfectly smooth, such as the surface of a bearing. In addition, the technique requires that the part be rotated around an axis substantially coincident with its main axis, which is time consuming and difficult to achieve in a test setting; it is slow to carry out because of the thread and part manipulations involved; and it is not suited for the automated quality-control needs of modern industrial manufacturing applications. Lastly, the measurement of motion of the string is inexact and highly susceptible to operator error, making the measurement non-repeatable and of insufficient accuracy for many modern applications. The present invention is directed at providing an optical approach that overcomes these drawbacks.

BRIEF SUMMARY OF THE INVENTION

In general, the invention lies in the idea of mapping a portion of the surface of a machined part with an optical profilometer, thereby generating a three-dimensional height map of that portion of the sample. Inasmuch as the part is known to be a continuous (in the Cauchy sense) three-dimensional surface with relatively small superficial grooves, its local shape can be considered to be analytically smooth with a well-defined (but otherwise point-wise variable) curvature. Furthermore, it is assumed that, at the macroscopic level, the presence of superficial grooves does not considerably distort the relative smoothness of the shape. Therefore, a conventional fitting algorithm is employed for a surface selected a-priori with a set of parameters to be determined from the mapped height data. Once the values of these parameters are determined, a preferred axial direction for this surface can be calculated with respect to which the orientation of the grooves can then be determined.

The simplest embodiment of this general idea can be considered to be the case of a perfect cylinder for which the preferred direction can be considered the cylinder's longitudinal axis. In this most simple case, a cylindrical fitting algorithm is used to find the best virtual cylindrical configuration that fits the map data obtained by optical profilometry. The orientation of the grooves in the map data is then compared to the longitudinal axis of such virtual cylinder to calculate its lead angle. As a second example, a parabolic surface can be imagined; in this case, a two-dimensional parabolic fit will be performed and the parameters related to the second power in "x" and "y" will uniquely define the preferred direction and the curvature at every point along this direction.

The approach of the invention advantageously does not require the measured part to be positioned in any particular way for its measurement and can be carried out rapidly without any additional manipulation other than the steps involved in conventional profilometry. The rest of the process is carried out by a processor that can be used to carry out all steps automatically, including the step of stopping the manufacture of the part when the lead angle is measured to be outside a predetermined tolerance range of the design parameter. Then the operator (or a machine) may remove the part from the production line as non-compliant for later re-manufacture, disposal, or re-classification as a lower-grade product.

More particularly, the invention takes advantage of the fact that the profile of the grooves in machined parts typically has a significant degree of periodicity from the machining process, thereby lending itself well to harmonic analyses, such as Fourier transforms, wavelet transforms, Hilbert transforms, or other related analyses. As an example, the two dimensional Fourier Transform of a surface with grooves having a perfectly sinusoidal pattern would produce two aligned peaks symmetrically placed with respect the DC component peak located at the origin, and all three peaks would lie on a line perpendicular to the grooves. Thus, the lead angle of the grooves is readily obtained by comparing the direction of this line with that of the axis of interest in the part. In addition, the integrated amplitude of the peaks and their surroundings can be used to determine the depth of the lead marks and their distance from the origin can be used to determine frequency. One skilled in the art will recognize that such a surface, where the groove pattern is purely sinusoidal, is just an idealization; normally, there would be multiple frequencies present in the pattern, but all of them would nonetheless be placed approximately along a straight line passing through the origin of the frequency plane. This line will always be oriented perpendicular to the direction of the grooves.

Various other aspects and advantages of the invention will become clear from the description that follows and from the novel features particularly recited in the appended claims. Therefore, to the accomplishment of the objectives described above, this invention consists of the features hereinafter illustrated in the drawings, fully described in the detailed description of the preferred embodiments, and particularly pointed out in the claims. However, such drawings and description disclose only some of the various ways in which the invention may be practiced.

DETAILED DESCRIPTION OF THE INVENTION

The term "preferred" axis is used herein to refer to an arbitrary axis selected for measuring the direction of manufactured grooves in a part. Typically, the preferred axis will be the main axis of the part. The term "lead angle" is the angle between the manufacture groove or grooves on the surface of a machined part and the normal to the preferred axis of the part (i. e., more precisely, the angle between the tangent line at any point of the helix defined by a groove and a line crossing such tangent that is perpendicular to the preferred axis of the part). For example, in the simple case of a cylindrical geometry, the preferred axis of the part would normally be the cylinder's main axis. As such, the lead angle is also the angle between a plane perpendicular to the preferred axis and the plane containing any one circular revolution of a groove. To the extent such an angle may be identified with different terms in the industry or otherwise (such as "secondary lead" or "microlead" in Europe), "lead angle" is intended to encompass all such other definitions for the purposes of this invention, as described and claimed. Finally, with reference to an action taken during the manufacture of parts measured according to the invention, "removing" a part from the manufacturing process is intended to encompass the physical removal of the part from the manufacturing line for the purpose of discarding or remanufacturing it as well as identifying the part as a lower-grade product.

While the preferred axis can be selected arbitrarily based on the geometry of the part, in the most general sense a mathematical criterion is preferably employed in order to define it. For example, in the case of a cylinder a fitting algorithm based on six parameters (two spatial angles, three coordinates of a fixed point, and the radius) can be employed to determine the best cylinder that would fit the mapped surface. Once these six parameters are determined, the prefered axis can be taken to be the axis of the cylinder defined by the parameters. The measured surface is then corrected to take out its curvature based on the curvature of the fitting algorithm, which is simply accomplished by subtracting the fitted cylinder from the measured surface. The resulting flattened surface, which contains the more detailed height information corresponding to the grooves in the surface, is then used to determine the direction of the grooves with respect to the cylinder's axis.

In a similar fashion, for a parabolic surface a parabolic fit can be performed using the well known equation $Ax^2+Bx+Cy^2+Dy+Exy+F$. Once the coefficients {A, B, C, D, E, F} are determined, the preferred axis of the surface can be chosen to be the one determined by the direction cosines (cos_x, cos_y) calculated from the following system of equations:

$$\begin{cases} A = \dfrac{\cos\_y^2}{2R} \\ C = \dfrac{\cos\_x^2}{2R} \\ \cos\_x^2 + \cos\_y^2 = 1 \end{cases} \quad (1)$$

where R is the radius of curvature (which is approximately equal to the radius of a cylinder fitted to that surface).

While these two examples are expected to be the ones most applicable to conventional products manufactured in a rotating process, it is possible that parts with geometries unsuitable for parabolic or cylindrical fit could be encountered. In such cases, the preferred axis would be calculated as the expected value of the locally determined preferred axis. The general procedure would preferably begin with expressing the surface as a vectorial function of two arbitrary parameters (u,v) in the following manner:

$$\vec{r} = \vec{r}(u,v) \Leftrightarrow \begin{cases} x = x(u,v) \\ y = y(u,v) \\ z = z(u,v) \end{cases} \quad (2)$$

At every point $P_1$ [described by the vector $\vec{r}(u_1, v_1)$] of the surface, the tangent plane can be defined as the plane that passes through $P_1$ and two other infinitely close surface points $P_2$ and $P_3$ and given by the equation:

$$\begin{cases} [(\vec{r}-\vec{r}_1)\vec{r}_u\vec{r}_v] = 0 \\ \vec{r}_u \equiv \dfrac{\partial \vec{r}}{\partial u} \\ \vec{r}_v \equiv \dfrac{\partial \vec{r}}{\partial v} \end{cases} \quad (3)$$

In the above expressions, $\vec{r}=\vec{r}(u,v)$ is the vector that describes each point in the tangent plane and the symbol [ ] represents the scalar triple product (box product) of any three vectors such that $[\vec{a}\,\vec{b}\,\vec{c}] \equiv \vec{a}\cdot(\vec{b}\times\vec{c})$.

In a similar manner, the normal $\vec{N}$ to the surface at any point $P_1$ is defined as the normal to the tangential plane at that point:

$$\vec{N} \equiv \dfrac{\vec{r}_u \times \vec{r}_v}{|\vec{r}_u \times \vec{r}_v|}. \quad (4)$$

Then, at any given point $\vec{r}(u,v)$ on the surface, the curvature ($\vec{k}_N$) of the normal section containing the adjacent surface point $\vec{r}(u,v)+d\vec{r}(u,v)$ will be given by:

$$\begin{cases} \vec{k}_N = -\dfrac{d\vec{r}\cdot d\vec{N}}{ds^2} \\ ds \equiv |d\vec{r}| \end{cases} \quad (5)$$

Except for the case of a perfect sphere, when $|\vec{k}_N|$ has the same value for all normal surfaces, there will exist two principal normal sections associated with the largest and the smallest value of the curvature $|\vec{k}_N|$. Thus, the locally preferred axis (at each point) can be defined in association with one of these two normal sections, which can be shown to be orthogonal to each other. Note that a similar manner for choosing a preferred direction at each point can be adopted based on the concept of a geodesic (or tangential curve vector) that follows the direction of zero curvature in the tangential plane. Finally, the preferred axis for the whole surface can be determined as the overall expected value of the locally determined preferred axes, usually by the method of weighted or non-weighted averaging.

As one skilled in the art will recognize, the previous particular examples of cylindrical and parabolic surfaces can be derived from this general approach. For example, in the case of a cylinder the two normal sections at every point will be respectively parallel with and perpendicular to the cylinder's axis. The direction parallel with the axis of the cylinder will yield a zero value for the curvature (or infinite radius), while the perpendicular direction will result in a maximal value of the curvature (with a radius similar to that of the cylinder). It is thus easy to see that the preferred axis of the cylinder can be taken to be the preferred direction at each point that coincides with the cylinder's axis.

Figure 1:
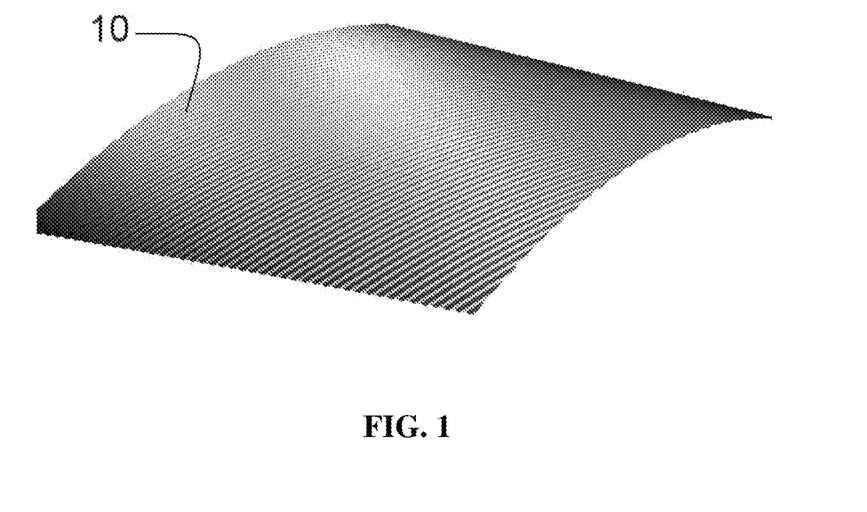
FIG. 1 is a magnified picture of a portion of the cylindrical surface of a shaft illustrating the machining grooves produced during the manufacture of the part.
Figure 2:
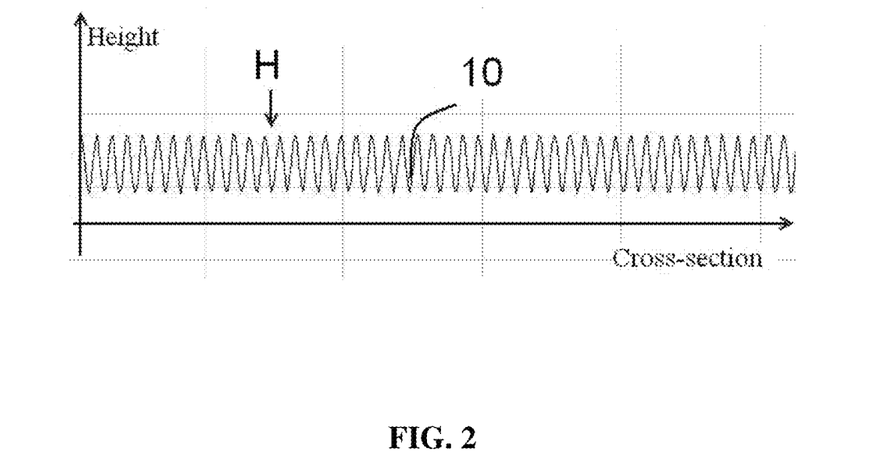
FIG. 2 illustrates the sinusoidal profile of the surface of a machined cylindrical part taken along a section that includes many turns of the grooves of interest.

For simplicity of illustration, the invention is described below with reference to a cylindrical symmetry, but it is understood that this shape is only one particular example of how the invention can be practiced, a conical or frusto-conical structure being other common examples of a rotated part. Referring to the figures, wherein like parts are referenced with the same numerals and symbols, FIG. 1 is a magnified picture of a portion of the cylindrical surface of a shaft showing the machining groove 10 produced during the manufacture of the part. The snapshot of a portion of a cylindrical surface shows multiple parallel grooves, but it is clear that in fact they belong to a single groove in the form of a helix produced by the cutting tool during manufacture. As illustrated in FIG. 2, any cross-sectional profile H of the surface of the part, so long as oriented sufficiently longitudinally to include numerous turns of the groove 10, will show a substantially sinusoidal height variation along the cross section of the part.

Figure 3:
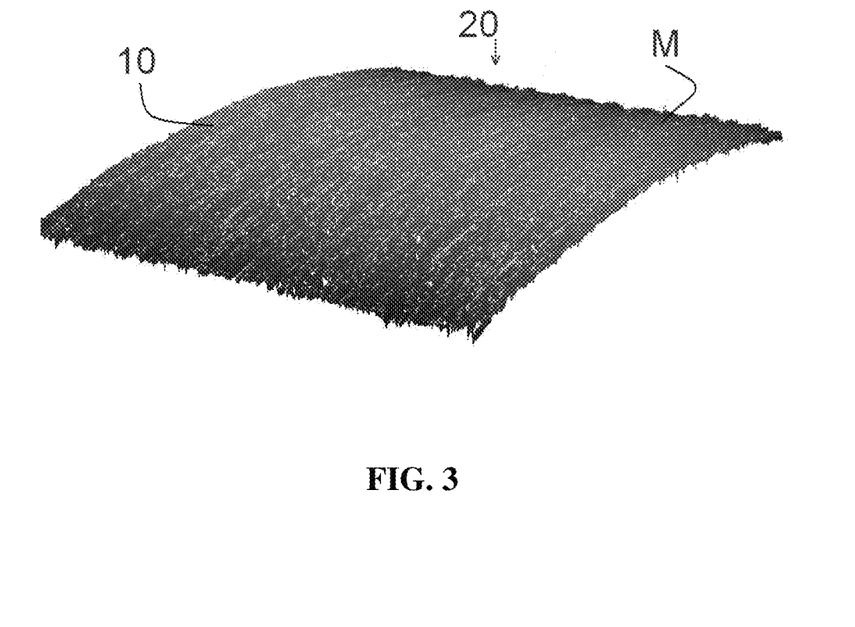
FIG. 3 illustrates the height map of a portion of the surface of a part being measured.

In FIGS. 1 and 2 the groove 10 and the profile H are shown without a reference to the axis of the part because the groove's orientation is not known. The objective of the measurement is to find the angle between the tangent to the groove at any point and line normal to the axis of the part at that same point. To that end, according to the invention, a swatch or section 20 of the part's surface is measured in conventional manner with an optical interferometer (or other conventional means, such as by atomic force profilometry) to produce a height map M, such as illustrated in FIG. 3. The orientation of the sample surface with respect to the measurement stage is not important because the measurement will produce a stand-alone three-dimensional map of the measured area, which is all that is needed to practice the invention. Any known profilometry technique can be used, as most appropriate depending on the size of the groove.

Figure 4:
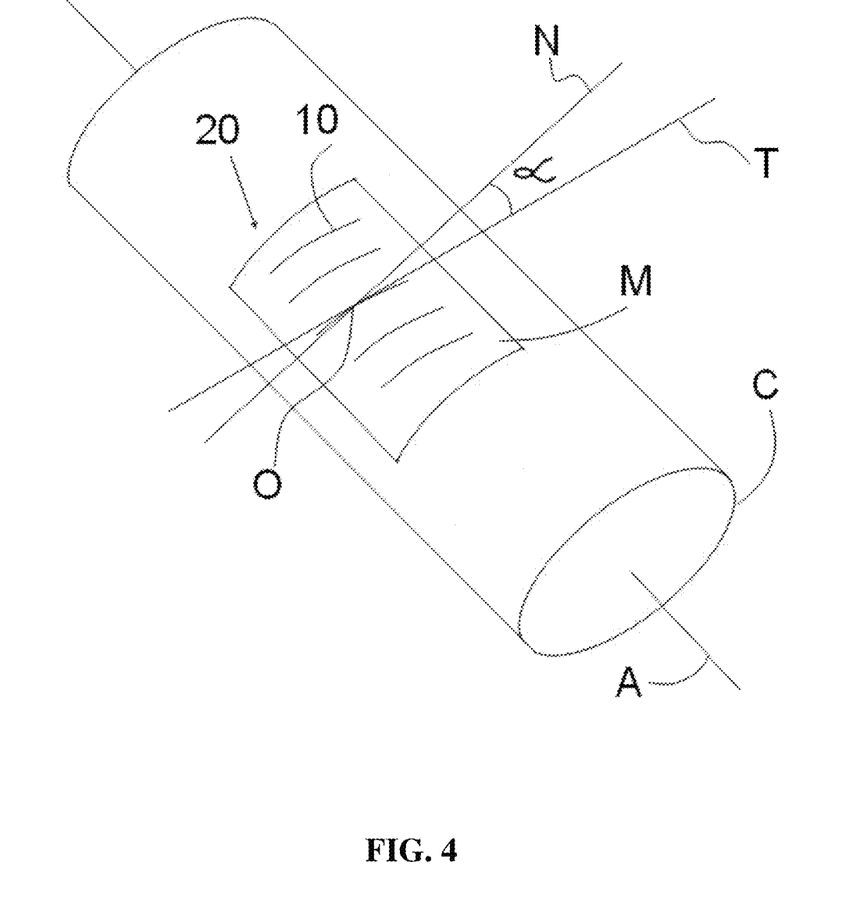
FIG. 4 illustrates the product of fitting the height data of FIG. 3 to a virtual cylindrical shape, thereby enabling the identification of the direction of the main axis of the cylindrical part being measured.

The height data produced by mapping the portion 20 of the surface are then fitted to a cylindrical shape to find the best cylinder size and orientation corresponding to the data. Based on the exact geometry of this virtual cylinder C, illustrated in FIG. 4, the exact orientation of the surface swatch 20 with respect to the cylinder from which it is derived is established, thereby also identifying the direction of its main axis A. Accordingly, the problem of the invention is now reduced to finding the angle α between the tangent T to the groove 10 at any point O of the groove and the line N passing through the point O that lies on the plane normal to the axis A. Alternatively expressed, the angle α is also the angle between the two lines (not shown in the figure) that are perpendicular to the tangent T and the line N at point O and lie on a plane parallel to the axis A.

Figure 5:
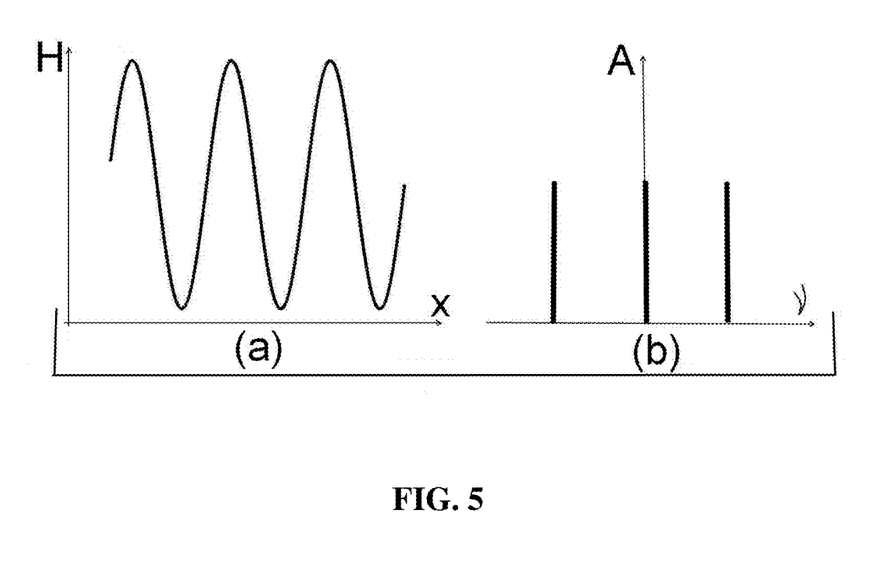
FIG. 5 is an illustration of the three peaks in FT frequency domain produced by a sinusoidal function, wherein the central peak is due to the DC component.
Figure 6:
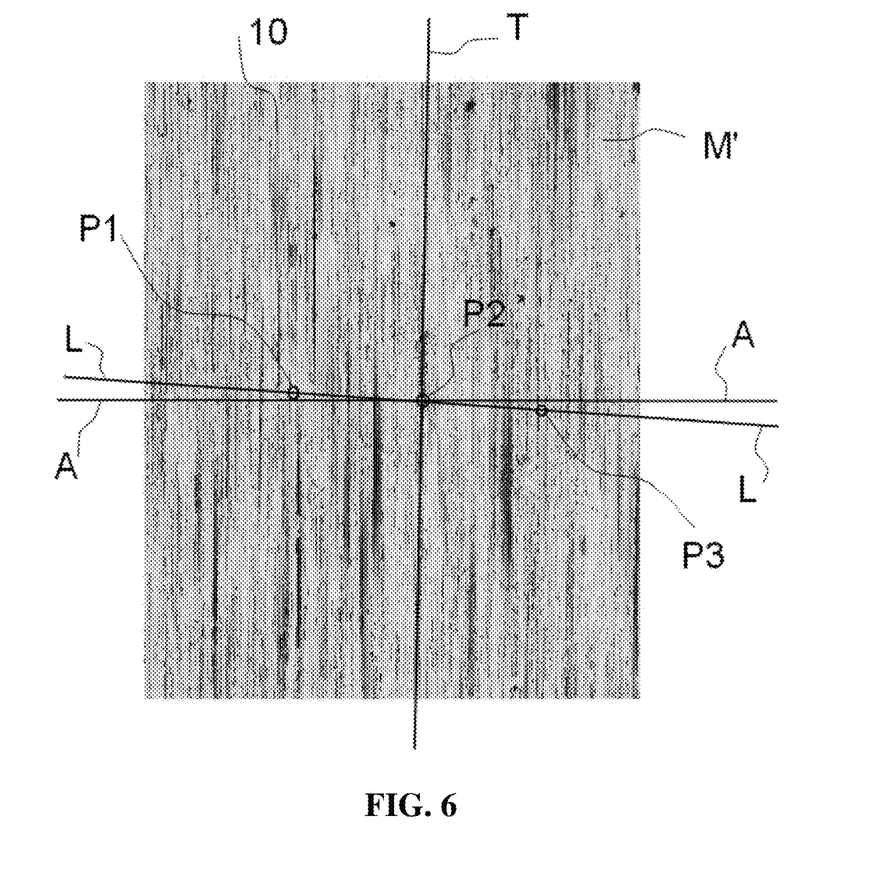
FIG. 6 illustrates the application of 2D FT analysis to the corrected height map of a portion of the surface of a machined part to identify the direction tangent to the groove introduced by the machining operation.
Figure 7:
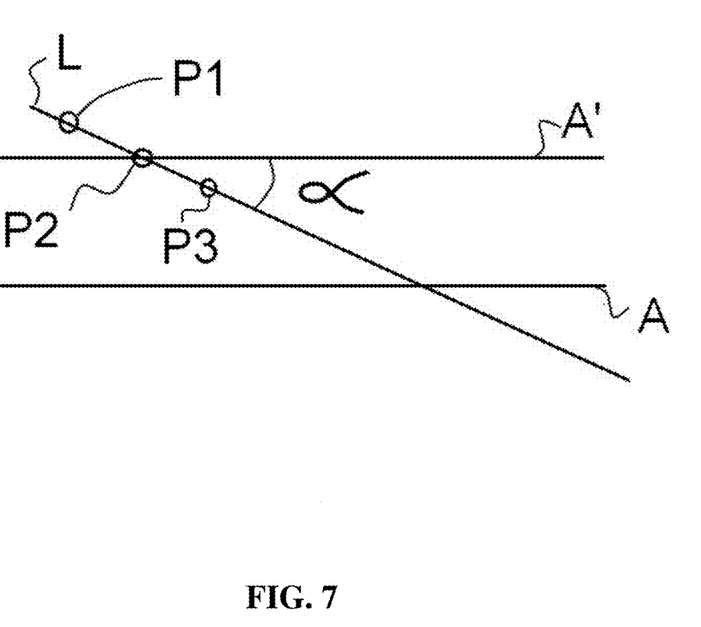
FIG. 7 illustrates the lead angle of the grooves of FIG. 6 in its geometric relation to the line tangent to the grooves and the axis of the part.

Prior to processing the height data corresponding to the groove 10 in the portion 20 of the test surface, the corresponding surface height data of the virtual cylinder C is subtracted from it, thereby flattening the surface to yield a plane map M' of the groove 10 (see FIG. 6). Because the cross-sectional profile H of the resulting map M' is substantially sinusoidal, as illustrated ideally in FIG. 5(*a*), its 2-D Fourier Transform yields three peaks in the transform frequency domain, as shown in FIG. 5(*b*), the central peak being due to the DC component. This property is used advantageously in the invention because it provides a straightforward approach to the determination of the lead angle of the groove 10 in the cylindrical part being measured. As those skilled in the art readily understand, the two-dimensional Fourier Transform of the height map M' will produce two FT domain peaks ($P_1$ and $P_3$), symmetrically placed with respect to the DC peak $P_2$ located at the origin, all aligned in a straight line L that is perpendicular to the tangent T to the groove 10, as illustrated in FIG. 6. Therefore, by comparing the direction of the line L passing through the peaks with the known direction of the part's axis A, the lead angle is determined as a matter of straightforward geometric calculation. As shown in FIG. 7, the lead angle α is simply the angle between the line L passing through the 2D FT peaks and the line A' parallel to the cylinder axis A that crosses the line L.

Note that in practice the only reference available is the CCD array of the instrument. Thus, the surface is measured to create a 3-D map through a conventional scan, the map is fitted to a cylindrical surface, and the direction of the axis of the cylinder is obtained with respect to the CCD array. Then the map of the part is corrected for curvature and the groove direction with respect to the CCD array is determined using a Fourier Transform or other harmonic analysis. Finally, by subtracting the lead angle (referenced to the CCD array) from the angle of the cylinder axis (referenced to the same CCD array), the true lead angle between the groove and the cylinder axis is derived.

Inasmuch as the sampling in the FT frequency domain is inversely proportional to the sample size, the sensitivity of the measurement is improved by the size of the sample used to create the map M by optical profilometry. Also, because of the imperfect sinusoidal form of the groove profile likely to be found on the machined part, the 2D FT analysis is preferably carried out according to ISO Standard 25178, which is directed to a refined analysis for textured surfaces. In addition to a large sample size giving the proper mathematical resolution, there are often large local variations in the parts to be measured, so that an area sufficient to provide a good representation of the part is needed.

There are several approaches for obtaining a sufficiently large sample size for good harmonic analysis. The most straightforward method is simply to measure a large enough region of the part to get adequate sampling; typically at least 4000 pixels are needed in each of the X and Y directions for a sensitivity of 0.001 degrees, which is a common industry goal. However, taking such a measurement in a single field of view requires a large camera array and potentially specialized optics to ensure that good data are obtained over much of the part.

A second option is to stitch together multiple measurements where each measurement is taken with a smaller field of view with fewer pixels than ultimately required. (See U.S. Pat. No. 6,987,570, for example.) For this method, each field of view must be precisely aligned to ensure that there is no skew in the directional machining marks. Therefore, good staging, part alignment, and a substantially cylindrical part may be required to achieve sufficient accuracy.

Yet another approach involves measuring, but not combining, multiple fields of view. If the array size of each field of view is insufficient to achieve the desired angular resolution for the lead angle or cylinder axis, it can be mathematically extended via interpolation, zero padding, or other techniques. As mentioned above, there are local variations in the machining marks on the parts. Thus, for improved accuracy and repeatability, many fields of view are typically analyzed and the cylinder direction and groove direction are averaged over all measurements to determine the true lead angle of the part. Advantageously, the technique of the present invention does not require different fields of view to be precisely aligned. Also, the user can choose to take measurements over the entire sample or only over areas of highest interest (such as concentrated on a sealing location) in order to maximize the relevance of the data to the ultimate quality-control objectives; that is, enabling the in-line recognition that the lead angle of a part under manufacture is outside the tolerances of design parameters and enabling the subsequent removal of the part from the production line.

A last advantage of this technique lies in the fact that it can also be used to identify problematic regions, thereby making it possible to eliminate them from consideration. For example, the parts may be contaminated with dirt, lubricants or other debris, or they may have defects from manufacturing or from subsequent damage. Calculating lead angles on such regions could be meaningless. However, such regions often have distinguishing characteristics (such as high roughness, features above or below a certain height threshold, low signal to noise ratio and thus fewer valid measurement points from the instrument) that can be used to identify the region as problematic and remove it from the final calculation of lead angle average. In addition, these results, as well as the value of the lead angle, may be used to pass or fail the part based on the number and problem severity of such regions.

We found that, when dealing with a cylindrical part with a sufficiently large radius, the invention can be practiced with acceptable results also by fitting the height map of the regions of interest to a parabolic surface rather than a cylindrical surface. Therefore, while not preferred, this simpler approach may be acceptable in some instance. In addition, as would be clear to one skilled in the art, the harmonic analysis of the invention enables not only the determination of the lead angle, but also the frequency and depth of the lead features. These parameters are often used as well to characterize the quality of a part during manufacturing.

Thus, a method has been described for measuring the lead angle of a part during the process of its manufacture so as to enable the detection of defects that warrant the removal of the part from the fabrication line according to predetermined design parameters, such as when the measured lead angle falls outside a predetermined range of acceptable values according to design parameters that correspond to acceptable manufacture tolerances. The removal may be manual, when an operator is alerted to the defect, or automatic, such as carried out by a computer operating on a production line machine.

Various changes in the details that have been described may be made by those skilled in the art within the principles and scope of the invention herein illustrated and defined in the appended claims. For example, the invention could be carried out similarly by applying one-dimensional FT analysis to various cross-sections of the map M' and finding the one providing the three closest peaks (i.e., two corresponding to the smallest frequency and one to the DC component, which in turns corresponds to the cross-section substantially normal to the groove). The invention could also be carried out in similar fashion by applying any other kind of harmonic analysis, such as wavelet transforms, Hilbert transforms, Riesz Transforms, or other related analysis tools, or using a correlation or an autocorrelation technique. This could be done, for example, by rotating a sinusoidal, cylindrical, or other pattern until achieving maximum correlation with the part, which would correspond to the angle being measured. The same approach could be followed by rotating an ideal cylinder and similarly maximizing correlation. (It is noted that the same result could be obtained by rotating the pattern until minimum correlation were achieved, in which case on skilled in the art would know to be aligned with a direction orthogonal to the preferred axis. Accordingly, this approach is intended to be covered by the invention as a correlation procedure.)

It is also noted that the invention could be practiced without the step of curvature removal from the original data, as described above, but using instead a 2-D digital filtering procedure in which the frequencies of interest (i.e., the grooves' frequency) would be the only ones kept for the final analysis. This technique in fact produces the same result as curvature removal procedure—that is, the surface "flattening" prior to the determination of the grooves' lead angle.

Thus, while the invention has been shown and described in what are believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and methods.

What is claimed is:

1. A method of detecting a defect for quality-control purposes in a lead angle of a groove in a surface of a part during a manufacturing process of the part, comprising the following steps:
    profiling a region of the surface with an optical profilometer to obtain a three-dimensional height map of said region of the surface;
    fitting said height map to a virtual three-dimensional geometric shape, thereby defining an orientation of a preferred axis thereof;
    determining said lead angle by comparing an orientation of said groove with said orientation of the preferred axis of the geometric shape; and
    removing said part from the manufacturing process when the lead angle falls outside a predetermined range of acceptable design values;
    wherein said profiling, fitting and determining steps are carried out with a processor.

2. The method of claim 1, wherein said part is a shaft.

3. The method of claim 1, wherein said part includes a frusto-conical structure.

4. The method of claim 1, wherein said groove is a product of machining the part.

5. The method of claim 1, wherein said determining step is carried out with a harmonic analysis of the height map.

6. The method of claim 5, wherein said harmonic analysis is a two-dimensional Fourier Transform analysis.

7. The method of claim 1, wherein said determining step is carried out with a correlation technique.

8. The method of claim 1, wherein said determining step is carried out with a 2-dimensional digital filtering technique.

9. The method of claim 1, wherein said lead angle is used to pass or fail the part based on a predetermined threshold value.

10. The method of claim 1, wherein said profiling, fitting and determining steps are repeated for multiple regions of the part's surface to calculate respective lead angles that are then averaged to obtain a final lead-angle value.

11. The method of claim 10, further including the steps of calculating a parameter of said multiple regions of the part's surface based on said profiling steps, and of disregarding a region when calculating said final lead-angle value if said parameter of the region exceeds a predetermined threshold value.

12. The method of claim 1, wherein said profiling step is repeated for multiple regions of the part's surface and the respective height maps thereof are stitched together for performing said fitting and determining steps.

13. The method of claim 1, wherein said geometric shape is a cylinder.

14. A method detecting a defect for quality-control purposes in a lead angle of a groove in a surface of a part during a manufacturing process of the part determining the lead angle of a groove on a part's surface, comprising the following steps:
    profiling a region of the surface with an optical profilometer to obtain a three-dimensional height map of said region of the surface;
    defining an orientation of a preferred axis of the part based on an expected value of locally determined preferred axes;
    determining said lead angle by comparing an orientation of said groove with said orientation of the preferred axis of the part; and
    removing said part from the manufacturing process when the lead angle falls outside a predetermined range of acceptable design values;
    wherein said profiling, defining and determining steps are carried out with a processor.

15. The method of claim 14, wherein said part is a shaft.

16. The method of claim 14, wherein said groove is a product of machining the part.

17. The method of claim 14, wherein said determining step is carried out with a harmonic analysis of the height map.

18. The method of claim 17, wherein said harmonic analysis is a two-dimensional Fourier Transform analysis.

19. The method of claim 14, wherein said determining step is carried out with a correlation technique.

20. The method of claim 14, wherein said determining step is carried out with a 2-dimensional digital filtering technique.

21. The method of claim 14, wherein said lead angle is used to pass or fail the part based on a predetermined threshold value.

22. The method of claim 14, wherein said profiling, fitting and determining steps are repeated for multiple regions of the part's surface to calculate respective lead angles that are then averaged to obtain a final lead-angle value.

23. The method of claim 22, further including the steps of calculating a parameter of said multiple regions of the part's surface based on said profiling steps, and of disregarding a region when calculating said final lead-angle value if said parameter of the region exceeds a predetermined threshold value.

24. The method of claim 14, wherein said profiling step is repeated for multiple regions of the part's surface and the respective height maps thereof are stitched together for performing said fitting and determining steps.

25. The method of claim 14, wherein said geometric shape is a cylinder.

26. Non-transitory computer readable medium containing computer instructions stored therein for causing a computer processor to perform the steps of detecting a defect for quality-control purposes in a lead angle of a groove in a surface of a part during a manufacturing process of the part by profiling a region of the surface with an optical profilometer to obtain a height map of said region of the surface, fitting said height map to a virtual three-dimensional geometric shape, thereby defining an orientation of a preferred axis thereof, determining said lead angle by comparing an orientation of said groove with said orientation of the preferred axis of the geometric shape; and automatically removing said part from said manufacturing process when said lead angle falls outside a predetermined range of acceptable design values.

27. Non-transitory computer readable medium containing computer instructions stored therein for causing a computer processor to perform the steps of detecting a defect for quality-control purposes in a lead angle of a groove in a surface of a part during a manufacturing process of the part by profiling a region of the surface with an optical profilometer to obtain a height map of said region of the surface, defining an orientation of a preferred axis of the part based on an expected value of locally determined preferred axes, determining said lead angle by comparing an orientation of said groove with said orientation of the preferred axis of the part; and automatically removing said part from said manufacturing process when said lead angle falls outside a predetermined range of acceptable design values.

\* \* \* \* \*